United States Patent [19]

Hong-Yue

[11] Patent Number: 4,544,551

[45] Date of Patent: Oct. 1, 1985

[54] ANTIPEPTIC ULCER COMPOSITION

[76] Inventor: Du Hong-Yue, No. 10 La. 48, Teh-Cheng St., Hsin-Chu Hsien, Taiwan

[21] Appl. No.: 350,865

[22] Filed: Feb. 22, 1982

Related U.S. Application Data

[63] Continuation of Ser. No. 854,549, Nov. 25, 1977, abandoned.

[30] Foreign Application Priority Data

Nov. 30, 1976 [GB] United Kingdom ............... 49885/76

[51] Int. Cl.$^4$ ............................................... A61K 33/26
[52] U.S. Cl. ................................................... 424/147
[58] Field of Search ........................................ 424/147

[56] References Cited

PUBLICATIONS

"The Dispensatory of the United States of America", 25th Ed., J. B. Lippincott Company, Phila., pp. 337, 565, 619.
Soine et al., "Rogers' Inorganic Pharmaceutical Chemistry", pp. 616–619, Lea and Febiger (1961).

Primary Examiner—Frederick E. Waddell
Attorney, Agent, or Firm—Lilling & Greenspan

[57] ABSTRACT

An antipeptic ulcer composition comprising ferrous sulfate, clove, and licorice.

9 Claims, No Drawings

ANTIPEPTIC ULCER COMPOSITION

This is a continuation, of application Ser. No. 854,549, filed Nov. 25, 1977, now abandoned.

The present invention relates to an antipeptic ulcer composition. More particularly, it provides an antipeptic ulcer composition comprising, ferrous sulfate, clove and optionally licorice herebelow referred as agents A, B and C, respectively.

The agent A, ferrous sulfate, is commonly known as a treatment for iron deficiency; the agent B, clove, is used as a carminative and a flavor; and the agent C, licorice, is considered to possess demulcent, expectorant and laxative properties and is used considerably as a flavoring agent.

In the recent years, the extracts of licorice with various solvents have been employed in treating peptic ulcer, such as carbenoxolone, glycyrrhetic acid (K2) and FM100. But the composition according to the present invention shows a great deal of difference from them. Besides, there has been no one using agent A or both A and B for antipeptic ulcer composition.

The present inventor has been carrying out research on various compositions of agents A, B and C. It is found no curative effect when merely use agents A and C. A composition using A and B, herebelow referred as CD, indeed has some curative effect. Most of all, a composition using A, B and C herebelow referred as CD1, shows excellent synergistic cooperative action in treating peptic ulcer. The mechanism in the curative action of said compositions CD or CD1 has not been clarified yet, but it seems to be very different from that of antacid or anticholinergic drug.

The curative test of CD1 as described below shows that CD1 is much more effective than antacid, antipeptic agent (carrageenin), and anticholinergic drug (atropine sulfate). The curative ratio of CD1 even exceeds that of the most effective drug FM100.

The antipeptic ulcer compositions of the present invention CD and CD1 are prepared by compounding agents A, B and A, B, C respectively. When compositions of the present invention are administered as antipeptic ulcer compositions, it is advantageous to administer them as tablets, powders capsules or granules. The pharmaceutically acceptable excipients which can be used for said purpose are corn starch, or starch paste.

The animal test procedures are like those in acetic acid ulcer (so-called intractible ulcer). The details of the experimental procedures can be obtained with reference to Jap. J. Pharmacology 19.418, 1969 by Takagi. K.

In the experiments according to the present invention, male Wistar rats weighing 200–230 gm were laparatomized under ether anesthesia; and 0.05 ml of 30% acetic acid solution was injected into the subserosal layer in the glandular stomach. Then the abdomen was closed and the rats were fed normally. CD1 or CD suspended in 0.5% C.M.C. solution was administered orally twice a day. The control animals were treated with the vehicle alone. The animals were sacrificed 15 days after said operation to observe the curative ratio of the ulcers, and the results are summarized below as examples and tables.

EXAMPLE I

A composition CD chosen in 88% of agent A and 12% of agent B is tested as an example under procedures of acetic acid ulcer mentioned above. And we obtained the results shown herebelow in Table I.

TABLE I

| Treatment | Administration time | No. of rats | Ulcer Index ± SE (mm$^2$) | Curative ratio | P value |
|---|---|---|---|---|---|
| Control | 15 days | 10 | 16.2 ± 1.6 | | |
| CD:80 mg/kg | 15 days | 7 | 12.6 ± 2.3 | 22.4% | >0.2 |
| FM 100:200 mg/kg | 15 days | 10 | 9.5 ± 1.9 | 41.2% | <0.02 |

Remarks: The ulcer index is defined as the sum of the ulcer area which was calculated by multiplying the length by the width of each ulcer.

EXAMPLE II

A composition CD1 chosen in 68% of agent A, 9% of agent B and 23% of agent C is tested as an example under procedures of acetic acid ulcer mentioned above. We obtained the results shown herebelow in Table II.

TABLE II

| Treatment | Administration time | No of rats | Ulcer Index ± SE (mm$^2$) | Curative ratio | P value |
|---|---|---|---|---|---|
| Control | 15 days | 7 | 21.7 ± 2.0 | | |
| CD1:100 mg/kg | 15 days | 7 | 9.6 ± 1.7 | 55.7% | <0.001 |

For the purpose of comparison and reference, the curative ratio of several conventional drugs by 15 days administration were as follows:

| No. | Drugs | Curative ratio |
|---|---|---|
| 1. | Aluminum silicate (1000 mg/kg per o.s.) | 11.4% |
| 2. | Atropine Sulfate (20 mg/kg s.c.) | 26.7% |
| 3. | Chlorophyl Cu—Na (500 mg/kg per o.s.) | 39.8% |
| 4. | Glycyrrhetic acid (K$_2$) (700 mg/kg per o.s.) | 33.7% |

Remarks: Data from Jap. J. Pharmacol. 19.418 (1969).

Besides, a seasonal variation of experimental results in FM100 are listed in Table III.

TABLE III

| Exp. No. | Administration time | Treatment | No. of rats | Ulcer Index ± SE (mm$^2$) | Curative ratio |
|---|---|---|---|---|---|
| 1 | 10 days | Control | 10 | 20.9 ± 3.7 | 32% |
|   |   | FM 100:400 mg/kg | 10 | 14.3 ± 2.0 | |
| 2 | 10 days | Control | 11 | 19.2 ± 2.6 | 38% |
|   |   | FM 100:200 mg/kg | 12 | 11.8 ± 1.4 | |
| 3 | 10 days | Control | 12 | 19.5 ± 3.1 | 41% |
|   |   | FM 100:200 mg/kg | 11 | 11.4 ± 1.9 | |
| 4 | 10 days | Control | 8 | 33.1 ± 4.3 | |
|   |   | FM 100:200 mg/kg | 10 | 15.1 ± 1.6 | 54% |
|   |   | 400 mg/kg | 10 | 16.6 ± 2.6 | 50% |
| 5 | 15 days | Control | 18 | 22.6 ± 4.0 | 50% |
|   |   | FM 100:400 mg/kg | 16 | 11.4 ± 2.6 | |

Remarks: Data from Jap. J. Pharmacol. 21.832 (1971).

Therefore, it is concluded that CD1 has an excellent curative ratio in therapeutic effect on chronic peptic ulcer. Besides, it also has less side effects than other agents.

What I claim is:

1. An orally administered antipeptic ulcer composition comprising a therapeutically effective amount of ferrous sulfate, clove and licorice.

2. The antipeptic ulcer composition of claim 1, in conjunction with a pharmaceutically acceptable carrier.

3. The antipeptic ulcer composition of claim 2, in the form of tablets or powders.

4. The antipeptic ulcer composition of claim 2, wherein the ratio of ferrous sulfate to clover is 68–88:4–12, respectively, by weight.

5. The antipeptic ulcer composition of claim 1, consisting of 68 weight % ferrous sulfate, 9 weight % clove and 23 weight % licorice.

6. A method for treating a peptic ulcer by orally administering a composition comprising a therapeutically effective amount of ferrous sulfate, clove and licorice.

7. The method of claim 6, wherein the ratio of ferrous sulfate to clove is 68–88:9–12, respectively, by weight.

8. The method of claim 6, wherein the composition consists of 68 weight % ferrous sulfate, 9 weight % clove and 23 weight % licorice.

9. The method of claim 6, wherein said composition is administered in conjunction with a pharmaceutically effective carrier.

* * * * *

UNITED STATES PATENT AND TRADEMARK OFFICE
CERTIFICATE OF CORRECTION

PATENT NO. : 4,544,551

DATED : October 1, 1985

INVENTOR(S) : Du Hong YUE

It is certified that error appears in the above—identified patent and that said Letters Patent is hereby corrected as shown below:

Column 3, line 5,          Change "68-88:4-12" to --68-88:9-12--.

Signed and Sealed this

First Day of April 1986

[SEAL]

Attest:

DONALD J. QUIGG

Attesting Officer      Commissioner of Patents and Trademarks